(12) United States Patent
Chiang (10) Patent No.: US 10,434,130 B2
(45) Date of Patent: Oct. 8, 2019

(54) HYDROLYSATE OF WATER EXTRACT OF SYZYGIUM SAMARANGENSE, AND PREPARATION PROCESS AND USE THEREOF

(71) Applicant: MHBT CO., LTD., Douliou, Yunlin County (TW)

(72) Inventor: Chun-Hui Chiang, Douliou (TW)

(73) Assignee: MHBT CO., LTD., Douliou, Yunlin County (TW)

( * ) Notice: Subject to any disclaimer, the term of this patent is extended or adjusted under 35 U.S.C. 154(b) by 386 days.

(21) Appl. No.: 15/409,103

(22) Filed: Jan. 18, 2017

(65) Prior Publication Data

US 2018/0104297 A1  Apr. 19, 2018

(30) Foreign Application Priority Data

Oct. 13, 2016  (TW) .............................. 105133083 A (51) Int. Cl.
| | |
|---|---|
| *A61K 36/61* | (2006.01) |
| *A61Q 19/02* | (2006.01) |
| *A61Q 19/00* | (2006.01) |
| *A61Q 19/08* | (2006.01) |
| *C12N 9/50* | (2006.01) |
| *A61K 8/66* | (2006.01) |
| *A61K 8/9789* | (2017.01) |
| *A61L 26/00* | (2006.01) |

(52) U.S. Cl.
CPC ................ *A61K 36/61* (2013.01); *A61K 8/66* (2013.01); *A61K 8/9789* (2017.08); *A61L 26/0057* (2013.01); *A61Q 19/00* (2013.01); *A61Q 19/02* (2013.01); *A61Q 19/08* (2013.01); *C12N 9/63* (2013.01); *C12Y 304/22033* (2013.01); *A61K 2236/19* (2013.01); *A61K 2236/331* (2013.01); *A61K 2236/53* (2013.01); *A61K 2800/74* (2013.01)

(58) Field of Classification Search
None
See application file for complete search history.

(56) References Cited

FOREIGN PATENT DOCUMENTS

| CN | 102228207 | * | 11/2011 |
|---|---|---|---|
| CN | 103349324 | * | 10/2013 |
| CN | 103371401 | * | 10/2013 |
| CN | 107970278 | * | 5/2018 |
| TW | I465258 B | | 12/2014 |

OTHER PUBLICATIONS

Sulaiman S. et al. Antioxidant and Alpha Glucosidase Inhibitory Activities of 40 Tropical Juices from Malaysia . . . J of Agricultural and Food Chemistry 62(39)9576-9585 Oct. 2014. (Year: 2014).*
Yi-Zhen Chen, "Application of Extracts from Wax Apple Flowers on Antioxidantion", thesis for the Degree of Master, Jul. 30, 2009, 69 pages.
Pei-Wen Lo, "Evaluation of the Antioxidative and Free Radical-scavenging Activity of Several Taiwan Unique Fruits", thesis for the Degree of Master, 2001, 109 pages.

* cited by examiner

*Primary Examiner* — Ralph J Gitomer
(74) *Attorney, Agent, or Firm* — Hamre, Schumann, Mueller & Larson, P.C.

(57) ABSTRACT

Disclosed herein are a hydrolysate of water extract of *Syzygium samarangense* and a preparation process thereof. Also disclosed herein is a composition which comprises the hydrolysate of water extract of *Syzygium samarangense*. The composition is suitable for whitening skin, enhancing the moisture-retaining capacity of skin, improving wound healing, and reducing oxidative stress.

19 Claims, 5 Drawing Sheets

HYDROLYSATE OF WATER EXTRACT OF SYZYGIUM SAMARANGENSE, AND PREPARATION PROCESS AND USE THEREOF

CROSS-REFERENCE TO RELATED APPLICATION

This application claims priority of Taiwanese Patent Application No. 105133083, filed on Oct. 13, 2016.

FIELD

The present disclosure relates to a hydrolysate of water extract of *Syzygium samarangense* and a preparation process thereof. The present disclosure also relates to use of the aforesaid hydrolysate for whitening skin, enhancing the moisture-retaining capacity of skin, improving wound healing, and reducing oxidative stress.

BACKGROUND

Skin is the largest protective barrier for the human body, and is able to prevent water loss, entering of pathogens, and damages by various harmful environments. Heavy exposure to ultraviolet (UV), ionizing radiation, drugs, or xenobiotics induces generation of reactive oxygen species (ROS) and free radicals in skin. When accumulating ROS and free radicals exceed the antioxidant capacity of cells or tissues, oxidative stress occurs. Particularly, ROS and free radicals react with cell components (including DNA, proteins, and lipids), such that skin is adversely influenced. It has been reported that ROS and free radicals not only play an important role in melanogenesis, but also lead to delay of wound healing (Kim Y. J. and Yokozawa T. (2009), *Biol. Pharm. Bull.*, 32:1155-1159; and Kurahashi T. and Fujii J. (2009), *J. Dev. Biol.*, 3:57-700).

Melanogenesis is a process where tyrosine in melanocytes is converted to melanin under catalysis of tyrosinase and a series of oxidation-reduction reactions. Melanogenesis is normally induced by UV radiation (particularly UV-B). When skin is exposed to UV radiation, the ROS and free radicals generated in keratinocytes induce expression of tumor protein 53 (p53), thereby giving rise to expression of the proopiomelanocortin gene (POMC gene) and releasing POMC-derived peptides such as α-melanocyte stimulating hormone (α-MSH) and adrenocorticotropic hormone (ACTH). Further, the tyrosine gene in melanocytes is expressed, such that a large amount of melanin accumulates on skin.

When skin damage (for example, scald, trauma, surgical injury, contusion, etc.) leads to wound, an inflammatory response is triggered at the wound site. A tremendous amount of ROS and free radicals are released to assist immune cells in fighting against pathogens. However, excess ROS and free radicals cause damage to the tissues surrounding wound. In the wound healing process, fibroblasts aggregate at the wound site to proliferate and to release growth factors, thereby resulting in angiogenesis, epithelialization, collagen remolding, and so forth. Excess ROS and free radicals not only inhibit angiogenesis, but also inactivate the enzymes involved in signal transduction pathways, such that wound healing is hindered.

In recent years, the demand for skin whitening, moisturizing, facilitation of wound healing, and antioxidation have been increasing. Particularly, use of natural ingredients, which do not cause undesired harmful side effects on skin, has become a trend for the field of aesthetic medicine. Therefore, to satisfy such great demand, researchers in the health care industry and cosmetic industry endeavor to look for safe active ingredients, which are effective in whitening, moisturizing, wound healing, and antioxidation, from traditional Chinese medicines (TCM) or plants.

*Syzygium samarangense* (common name: wax apple; Pinyin: lian wu) is a perennial evergreen tree which belongs to the family Myrtaceae and the genus *Syzygium*, and which has opposite simple leaves that are elliptical in shape, axillary flowers that have pale yellow corolla, and berries that are obconical in shape. *Syzygium samarangense* is distributed over Taiwan, Indonesia, Philippines, Malaysia, and so forth. The common cultivars of *Syzygium samarangense* fruits include dark red cultivars, pale red cultivars, "Black Pearl", "Black King Kong", "Black Diamond", etc. *Syzygium samarangense* fruits are frequently used. In the field of Chinese fold medicine, *Syzygium samarangense* fruits are used for lung nourishing, cough suppression, sputum reduction, blood cooling, and induction of astringency. In addition, *Syzygium samarangense* fruits are considered to be effective in relieving fever, promoting dieresis, and reducing mental strain.

The application of the *Syzygium samarangense* extract in the pharmaceutical field has been studied. For instance, as reported in the thesis written by Pei-Wen Lo from the Department of Nutrition and Food Science at Fu-Jen Catholic University ("Evaluation of the Antioxidative and Free Radical-scavenging Activity of Several Taiwan Unique Fruits"), the antioxidation efficacy regarding the *Syzygium samarangense* fruit and other types of fruits was investigated. Specifically, 14 types of fruits (fruits of *Citrus sinensis* Osbeck, *Citrus tankan* Hayata, *Citrus grandis* (L) Osbeck, *Citrus grandis* Osbeck, *Citrus micro carpa*, *Fragaria ananassa* Duch, *Hylocereus undatus*, *Syzygium samarangense*, *Diospyros kaki* L., *Mangifera indica* L., *Carica papaya* L., *Zityphus jujuba*, *Averrhoa carambola* L., and *Psidium guajava* L.) were subjected to lyophilization and grinding to form powder. 10 g of powder of a respective fruit was subjected to a 6-hour extraction treatment using 100 mL of methanol, followed by a filtration treatment with a filter paper. The resulting filtrate was subjected to concentration and drying. Thus, 14 methanol extracts of fruit were obtained, and were tested for the antioxidation efficacy. The experimental results indicate that the aforesaid 14 methanol extracts of fruit exhibit different levels of activities in different tests. Particularly, via the test for the α,α-diphenyl-β-picryhydrazyl (DPPH) radical scavenging ability, it was found that the methanol extract of a fruit material (containing a peel and a pulp) of *Syzygium samarangense* has the worst DPPH radical scavenging ability. Furthermore, the result of the test for the ability to inhibit superoxide anion generation reveals that the methanol extract of the fruit material of *Syzygium samarangense* is not able to inhibit superoxide anion generation, but instead induces superoxide anion generation.

In addition, as described in the thesis written by Yi-Zhen C en from the Institute of Cosmetic Science at Chia Nan University of Pharmacy & Science ("Application of Extracts from Wax Apple Flowers on Antioxidantion") the antioxidation efficacy and tyrosinase inhibition ability regarding the *Syzygium samarangense* flower were examined. Specifically, 50 g of dry powder of a *Syzygium samarangense* flower was subjected to a one-hour extraction treatment with 500 mL of 80% methanol, and 50 g of dry powder of a *Syzygium samarangense* flower was subjected to a one-hour extraction treatment with 500 mL of water. Subsequently, a filtration treatment was conducted using a filtration paper. The resulting two filtrates were subjected to concentration and lyophilization, such that a methanol extract of *Syzygium samarangense* flower and a water extract of *Syzygium samarangense* flower were obtained. The aforesaid two extracts were tested for the antioxidation efficacy and tyrosinase inhibition activity. In most of the tests for the antioxidation efficacy (i.e. the tests for the superoxide anion scavenging ability, lipid peroxidation inhibition activity, and ferrous ion chelating ability), it was found that the antioxidation efficacy of the aforesaid water extract is better than that of the aforesaid methanol extract. However, the results show that the tyrosinase inhibition ability of the aforesaid methanol extract is significantly better than that of the water extract.

TW 1465258 discloses an ethanol extract of *Syzygium samarangense* flower (which has skin whitening and anti-aging effects) and a preparation process thereof. The aforesaid preparation process includes subjecting dry powder of *Syzygium samarangense* flower to an extraction treatment with 95% ethanol, subsequently conducting a filtration treatment, and subjecting the filtrate thus obtained to a concentration treatment. It was verfied from experiments that the aforesaid ethanol extract of *Syzygium samarangense* flower is effective in serving as an antioxidant, inhibiting tyrosinase, and facilitating collagen formation.

In spite of the aforesaid documents, the researchers in this field still endeavor look fora more satisfactory bioactive component from *Syzygium samarangense*. In a previous study, the applicants found that a water extract of a fruit material of *Syzygium samarangense* is slightly effective in inhibiting the activity of tyrosinase, enhancing the moisture-retaining capacity of skin, and improving would healing (such finding has never been published). In a further study, the applicants surprisingly observed that a hydrolysate, which is prepared by subjecting a water extract (obtained from a fruit material of *Syzygium samarangense*) to a hydrolysis treatment with bromelain, can more effectively inhibit the activity of tyrosinase, enhance the moisture-retaining capacity of skin, and improve wound healing compared to the water extract from which it is prepared. Thus, it is expected that a hydrolysate of water extract of *Syzygium samarangense* can serve as an active ingredient for a cosmetic or pharmaceutical composition.

SUMMARY

Therefore, in a first aspect, this disclosure provides a process for preparing a hydrolysate of water extract of *Syzygium samarangense*, which comprises:

subjecting a fruit material of *Syzygium samarangense* to an extraction treatment with water so as to obtain a water extract; and subjecting the water extract to a hydrolysis treatment with bromelain.

In a second aspect, this disclosure provides a hydrolysate of water extract of *Syzygium samarangense*, which is prepared by a process comprising:

subjecting a fruit material of *Syzygium samarangense* to an extraction treatment with water so as to obtain a water extract, and subjecting the water extract to a hydrolysis treatment with bromelain.

In a third aspect, this disclosure provides a composition comprising the aforementioned hydrolysate of water extract of *Syzygium samarangense*.

In a forth aspect, this disclosure provides a method for whitening skin, which comprises administering to a subject the aforementioned composition.

In a fifth aspect, this disclosure provides a method for enhancing the moisture-retaining capacity of skin, which comprises administering to subject the aforementioned composition.

In a sixth aspect, this disclosure provides a method for improving wound healing, which comprises administering to a subject the aforementioned composition.

In a seventh aspect, this disclosure provides a method for reducing oxidative stress, which comprises administering to a subject the aforementioned composition.

BRIEF DESCRIPTION OF THE DRAWINGS

Other features and advantages of the disclosure will become apparent in the following detailed description of the embodiments with reference to the accompanying drawings, of which.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs.

One skilled in the art will recognize many methods and materials similar or equivalent to those described herein, which could be used in the practice of the present disclosure. Indeed, the present disclosure is in no way limited to the methods and materials described.

In order to develop a skin care composition that is safe for long term use, the applicants have attempted to obtain extracts of *Syzygium samarangense* fruit using various methods. The applicants have further found that a hydrolysate, which is prepared by subjecting a water extract of *Syzygium samarangense* fruit to a hydrolysis treatment with bromelain, is more effective in performing ferrous ion chelation (i.e. serving as an antioxidant), inhibiting tyrosinase activity, enhancing the moisture-retaining capacity of skin, and improving wound-healing, compared to the water extract from which it is prepared.

Accordingly, the present disclosure provides a hydrolysate of water extract of *Syzygium samarangense* and a process for preparing the same. The hydrolysate of water extract of *Syzygium samarangense* according to the present disclosure is prepared by a process comprising:

subjecting a fruit material of *Syzygium samarangense* to an extraction treatment with water so as to obtain a water extract, and subjecting the water extract to a hydrolysis treatment with bromelain.

According to the present disclosure, the fruit material of *Syzygium samarangense* comprises a pulp of *Syzygium samarangense*. In some embodiments, the fruit material of *Syzygium samarangense* further comprises a peel of *Syzygium samarangense* and a seed of *Syzygium samarangense*.

According to the present disclosure, the fruit material of *Syzygium samarangense* may be obtained from *Syzygium samarangense* fruits of different cultivars. In some embodiments, the fruit material of *Syzygium samarangense* is obtained from one or more *Syzygium samarangense* fruits belonging to cultivars selected from Black Pearl, dark red cultivars, light red cultivars, pink cultivars (also known as Nanyang cultivars), Black Diamond, and Black King Kong. In an exemplary embodiment, the fruit material of *Syzygium samarangense* is obtained from a *Syzygium samarangense* fruit belonging to the Black Pearl cultivar.

According to the present disclosure, the fruit material of *Syzygium samarangense* may be obtained from *Syzygium samarangense* fruits having various fruit maturity. In certain embodiments, the fruit material of *Syzygium samarangense* is obtained from a young *Syzygium samarangense* fruit. In an exemplary embodiment, the fruit material of *Syzygium samarangense* is obtained from a young *Syzygium samarangense* fruit harvested after one-month of bloom.

According to the present disclosure, the fruit material of *Syzygium samarangense* to be extracted with water may be a fresh fruit material of *Syzygium samarangense*, or may be subjected to a pre-treatment selected from a drying treatment, a grinding treatment, a shredding treatment, a pulverizing treatment, and a combination thereof, prior to the extraction treatment with water.

According to the present disclosure, the extraction treatment with water may be conducted using technology well-known to those skilled in the art. For example, the extraction treatment with water may be conducted according to the method described in the thesis written by Yi-Zhen Chen from the Institute of Cosmetic Science at Chia Nan University of Pharmacy 8, Science (supra).

According to the present disclosure, the weight ratio of the fruit material of *Syzygium samarangense* to water ranges from 1:0.5 to 1:5. In an embodiment of this disclosure, the weight ratio of the fruit material of *Syzygium samarangense* to water is 1:1.25.

According to the present disclosure, the extraction treatment with water may be conducted at a temperature ranging from 35° C. to 65° C. In an embodiment of the present disclosure, the extraction treatment with water may be conducted at 50° C.

It should be noted that the conditions for the extraction treatment with water may vary with several factors (such as the pre-treatment of the fruit material of *Syzygium samarangense*, the weight ratio of the fruit material of *Syzygium samarangense* to water, etc.) so as to achieve a desired extraction result.

According to the present disclosure, the weight ratio of bromelain to the water extract ranges from 1:50 to 1:300. In an embodiment of the present disclosure, the weight ratio of bromelain to the water extract is 1:180.

According to this disclosure, the hydrolysis treatment with bromelain may be conducted at a temperature ranging from 30° C. to 60° C. for 3 hours to 6 hours. In an embodiment of the present disclosure, the hydrolysis treatment with bromelain is conducted at 45° C. for 4 hours.

It should be noted that the conditions for the hydrolysis treatment with bromelain may vary with several factors (such as the weight ratio of the water extract to bromelain, etc.,) so as to achieve the desired hydorlysis result.

According to the present disclosure, the preparation process for the hydrolysate of water extract of *Syzygium samarangense* may further comprise conducting a solid-liquid separation treatment after the hydrolysis treatment so as to remove a solid portion resulting from the hydrolysis treatment. The solid-liquid separation treatment may be conducted using technology well-known to those skilled in the art. Examples of the solid-liquid separation treatment include, but are not limited to, filtration, centrifugation and decantation. In an embodiment of the present disclosure, the solid-liquid separation treatment includes a centrifugation step and a subsequent filtration step.

The applicants have found that the hydrolysate of water extract of *Syzygium samarangense* according to the present disclosure have the biological effects described below.

First, it has verified via in vitro experiments that the hydrolysate of water extract of *Syzygium samarangense* according to the present disclosure is able to effectively inhibit tyrosinase activity. Therefore, the hydrolysate of water extract of *Syzygium samarangense* according to the present disclosure is expected to be effective in whitening skin.

As used herein, the terms "whitening skin", "lightening skin color", 'bleaching skin", "brightening skin", "lightening melanin", "inhibiting melanogenesis", and "inhibiting melanin synthesis" can be interchangeabily used.

Secondly, the results of the preliminary human tests done by the applicants show that the hydrolysate of water extract of *Syzygium samarangense* according to the present disclosure can effectively increase the water content of stratum corneum without incurring undesired side effects. Therefore, the hydrolysate of water extract of *Syzygium samarangense* according to this disclosure is expected to be useful in enhancing the moisture-retaining capacity of skin.

Thirdly, it has been proven via in vitro experiments that the hydrolysate of water extract of *Syzygium samarangense* according to the present disclosure is effective in improving the fibroblast-mediated wound closure. As such, it is contemplated that the hydrolysate of water extract of *Syzygium samarangense* according to this disclosure can be used in the improvement of wound healing.

Fourthly, it has been verified through in vitro experiments that the hydrolysate of water extract of *Syzygium samarangense* according to the present disclosure has excellent ferrous ion chelating ability. Accordingly, the hydrolysate of water extract of *Syzygium samarangense* according to the present disclosure can be used as an antioxidant for reducing oxidative stress.

Fifthly, due to the fact that the hydrolysate of water extract of *Syzygium samarangense* according to this disclosure has antioxidation activity, it can be predicted that the hydrolysate of water extract of *Syzygium samarangense* according to this disclosure may be effective in preventing and/or retarding skin aging.

As used herein, the term "retarding" refers to treating, reducing, alleviating, ameliorating, relieving, or controlling one or more clinical signs of a disease or disorder, and lowering, stopping, or reversing the progression of severity regarding the condition or symptom being treated.

As used herein, the term "skin aging" is intended to encompass naturally occurring intrinsic skin aging and extrinsic skin aging caused by environmental factors (such as UV radiation). The symptoms of skin aging include, but are not limited to, telangiectasia, thinner epidermis, skin atrophy, poor skin texture, dryness, wrinkle formation and pigmentary change (such as lentigines, freckles, hypopigmentation or hyperpigmentation), etc.

Therefore, the present disclosure provides a composition comprising the aforesaid hydrolysate of water extract of *Syzygium samarangense*, which is suitable for whitening skin, enhancing the moisture-retaining capacity of skin, improving wound healing, reducing oxidative stress, and preventing and/or retarding skin aging.

Further, the present disclosure provides the following methods employing the composition described above.

First, the present disclosure provides a method for whitening skin, which comprises administering to a subject the composition described above. An effective amount of the composition may be administered for a sufficient time until the skin of the subject is significantly whitened. The effective amount of the composition would not cause an adverse side effect to the skin of the subject.

According to the disclosure, the dosage and frequency of administration of the composition for whitening skin may vary with the following factors: the initial condition of the skin area to be subjected to the lightening of melanin, the route of administration, and the desired whitening effect to be achieved. For instance, the dosage of the composition for topical administration according to this disclosure may be 1-10 mg/cm$^2$ of the skin area, and may be administered one to three times per day. In certain embodiments, the dosage of the composition for oral administration may be 0.05-5 mg/Kg body weight, and may be administered one to three times per day.

Secondly, the present disclosure provides a method for enhancing the moisture-retaining capacity of skin, which comprises administering to a subject the composition described above. An effective amount of the composition may be administered for a sufficient time until the moisture-retaining capacity of the skin of the subject is significantly enhanced. The effective amount of the composition would not cause an adverse side effect to the skin.

According to the disclosure, the dosage and frequency of administration of the composition for enhancing the moisture-retaining capacity of skin may vary with the following factors: the initial condition of the skin area to be subjected to the enhancement of the moisture-retaining capacity, the route of administration, and the desired moisture-retaining effect to be achieved. For instance, the dosage of the composition for topical administration according to this disclosure may be 1-10 mg/cm$^2$ of the skin area, and may be administered one to three times per day. In certain embodiments, the dosage of the composition for oral administration may be 0.05-5 mg/Kg body weight, and may be administered one to three times per day.

Thirdly, the present disclosure provides a method for improving wound healing, which comprises administering to a subject the composition described above. An effective amount of the composition may be administered for a sufficient time until the wound area is significantly decreased. The effective amount of the composition would not cause an adverse side effect to the wound.

According to the disclosure, the dosage and frequency of administration of the composition for improving wound healing may vary with the following factors: the severity of the wound to be treated, the route of administration, and the desired healing effect to be achieved. For instance, the dosage of the composition for topical administration according to this disclosure may be 1-10 mg/cm$^2$ of the skin area, and may be administered one to three times per day. In certain embodiments, the dosage of the composition for oral administration may be 0.05-5 mg/Kg body weight, and may be administered one to three times per day.

Fourthly, the present disclosure provides a method for reducing oxidative stress, which comprises administering to a subject the composition described above. An effective amount of the composition may be administered to the subject for a sufficient time until the oxidative stress is significantly reduced. The effective amount of the composition would not cause adverse side effects to the subject.

According to this disclosure, the dosage and frequency of administration of the composition for reducing oxidative stress may vary depending on the following factors: the severity of the oxidative stress to be treated, the route of administration, and the desired antioxidation effect to be achieved. For instance, the dosage of the composition for topical administration according to this disclosure may be 1-10 mg/cm$^2$ of the skin area, and may be administered one to three times per day. The dosage of the composition for oral administration may be 0.05-5 mg/Kg body weight, and may be administered one to three times per day.

Fifthly, the present disclosure provides a method for preventing and/or retarding skin aging, which comprises administering to a subject the composition described above. An effective amount of the composition may be administered to the subject for a sufficient time until at least one symptom of skin aging is significantly improved. The effective amount of the composition would not cause adverse side effects to the subject.

According to the present disclosure, the dosage and frequency of administration of the composition for preventing and/or retarding skin aging may vary with the following factors: the severity of the symptom of skin aging to be treated, the route of administration, and the desired effect to be achieved. For instance, the dosage of the composition for topical administration according to this disclosure may be 1-10 mg/cm$^2$ of the skin area, and may be administered one to three times per day. In certain embodiments, the dosage of the composition for oral administration may be 0.05-5 mg/Kg body weight, and may be administered one to three times per day.

Due to the above-mentioned biological activities and safety regarding the hydrolysate of water extract of *Syzygium samarangense*, the composition comprising the same (which is suitable for whitening skin, enhancing the moisture-retaining capacity of skin, improving wound healing, reducing oxidative stress, and preventing and/or retarding skin aging) may be a pharmaceutical composition or a cosmetic composition.

The pharmaceutical composition according to the present disclosure can be formulated into a suitable dosage form for oral or topical administration using technology well known to those skilled in the art.

The pharmaceutical composition according to the present disclosure can additionally include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, preservatives, wetting agents, lubricants, diluents, absorption delaying agents, liposomes, sweetening agents, flavoring agents, coloring agents, etc. The choice and amount of the pharmaceutically acceptable carrier are within the expertise of those skilled in the art.

Examples of the oral dosage form include, but are not limited to, aseptic power, tablets, troches, lozenges, pellets, capsules, dispersible powder or granule, solutions, suspensions, emulsions, syrup, elixir, slurry, etc.

Examples of the topical dosage form include, but are not limited to, emulsions, gels, ointments, cream, patches, liniments, powder, aerosol, spray, lotions, serum, paste, foam, drops, suspensions, salve, bandages, etc.

In an exemplary embodiment of the present disclosure, the pharmaceutical composition is formulated into an external preparation by admixing the hydrolysate of water extract of *Syzygium samarangense* with a base that is well known and commonly used in the art.

According to this disclosure, suitable bases may include one or more of the following additives: water, alcohol, glycol, hydrocarbons (such as petroleum jelly and white petrolatum), wax (such as paraffin and yellow wax), preserving agents, antioxidants, surfactants, absorption enhancers, stabilizing agents, gelling agents (such as Carbopol®974P, microcrystalline cellulose and carboxymethylcellulose), active agents, humectants, odor absorbers, fragrance, ph adjusting agents, chelating agents, emulsifiers, occlusive agents, emollients, thickeners, solubilizing agents, penetration enhancers, anti-irritants, colorants, propellants, etc. The choice and amount of these additives are within the expertise of those skilled in the art.

The cosmetic composition according to the present disclosure may further include a cosmetically acceptable adjuvant that is widely employed in cosmetic-manufacturing technology. For instance, the cosmetically acceptable adjuvant may include one or more of the following agents: solvents, gelling agents, activating agents, preservatives, antioxidants, screening agents, chelating agents, surfactants, coloring agents, thickening agents, fillers, fragrance, and odor absorbents. The choice and amount of these additives are within the expertise of those skilled in the art.

The cosmetic composition of the present disclosure can be prepared using technology well known to a skilled artisan into the form of skincare or makeup products. Such form includes, but is not limited to, aqueous solutions, aqueous-alcohol solutions or oily solutions, emulsions, gel, ointments, cream, masks, patches, packs, liniment, powder, aerosol, spray, lotions, serum, paste, foam, suspensions, drops, mousse, sunblock, tonic water, foundation, eyeshadow, makeup remover products, soaps and other body cleansing products.

The cosmetic composition of the present disclosure can be used with at least one of the following external use agents: whitening agents (such as tretinoin, catechin, kojic acid, arbutin and vitamin C), humectants, anti-inflammatory agents, bactericides, ultraviolet absorbers, algal extracts (such as aloe extracts), skin nutrients, anesthetics, anti-acne agents, antipruritic, analgesic, antidermatitis agents, antihyperkeratolytic agents, anti-dry skin agents, antipsoriatic agents, antiaging agents, antiwrinkle agents, antiseborrheic agents, wound-healing agents, corticosteroid and hormone. The choice and amount of these agents are within the expertise of those skilled in the art.

The disclosure will be further described by way of the following examples. However, it should be understood that the following examples are solely intended for the purpose of illustration and should not be construed as limiting the disclosure in practice.

EXAMPLES

Example 1. Preparation of Hydrolysate of Water Extract of *Syzygium samarangense*

3 to 6 g of a fruit material (containing a peel, a pulp, and a seed) of *Syzygium samarangense* harvested from Fangliau Township (Pingtung County, Taiwan) was pulverized. The resulting pulverized product and water were mixed in a weight ratio of 1:1.25, followed by heating at 50° C. for 1 hour. A water extract of *Syzygium samarangense* (referred to as WESS hereinafter) was hence obtained.

Subsequently, 1600 U/g bromelain (NEO-ONE BIO-TECH CO., LTD.; Cat. No.: 1600 GD) and the WESS were mixed in a weight ratio of 1:180. The enzymatic hydrolysis reaction was allowed to proceed for 4 hours at 45° C. The reaction mixture thus obtained was subjected to centrifugation, followed by collecting the resulting supernatant. Filters with pore sizes of 5 μm, 1 μm, and 0.5 μm (Tech Seed Enterprise Co., Ltd.; Cat. Nos.: PureMax, SCB2000-001, and SP2000-00A) were used sequentially to conduct filtration. The resulting filtrate was subjected to lyophilization, such that a hydrolysate of water extract of *Syzygium samarangense* (referred to as HWESS hereinafter) in lyophilized powder form was obtained.

In addition, for the purpose of comparison with the HWESS, the WESS was also subjected to the centrifugation, filtration, and lyophilization treatments described above so as to convert the WESS into powder form.

Example 2. HPLC Analysis for Hydrolysate of Water Extract of *Syzygium samarangense*

In order to determine the major components of the HWESS according to the present disclosure, the HWESS obtained in Example 1 was dissolved in distilled deionized water so as to prepare a test sample having a HWESS concentration of 1 mg/mL. The test sample was subjected to a HPLC (high performance liquid chromatography) analysis.

The HPLC instruments employed are as follows: HP Agilent 1100 series HPLC System equipped with a UV-Vis detector and a C18 column (Purospher® STAR RP-18, Cat. No.: 150359, size: 250 mm×4.6 mm).

The HPLC operating conditions applied are described as follows. The mobile phase is acetonitrile/deionized water (100:0, v/v), and the flow rate of the mobile phase is 0.7 mL/min. The gradient elution with the mobile phase was conducted for 35 minutes as follows: acetonitrile was decreased from 100% to 90% during 0-10 minutes, was decreased from 90% to 80% during 10-30 minutes, was increased from 80% to 100% at 30 minute, and was maintained at 100% during 30-35 minutes.

Figure 1:
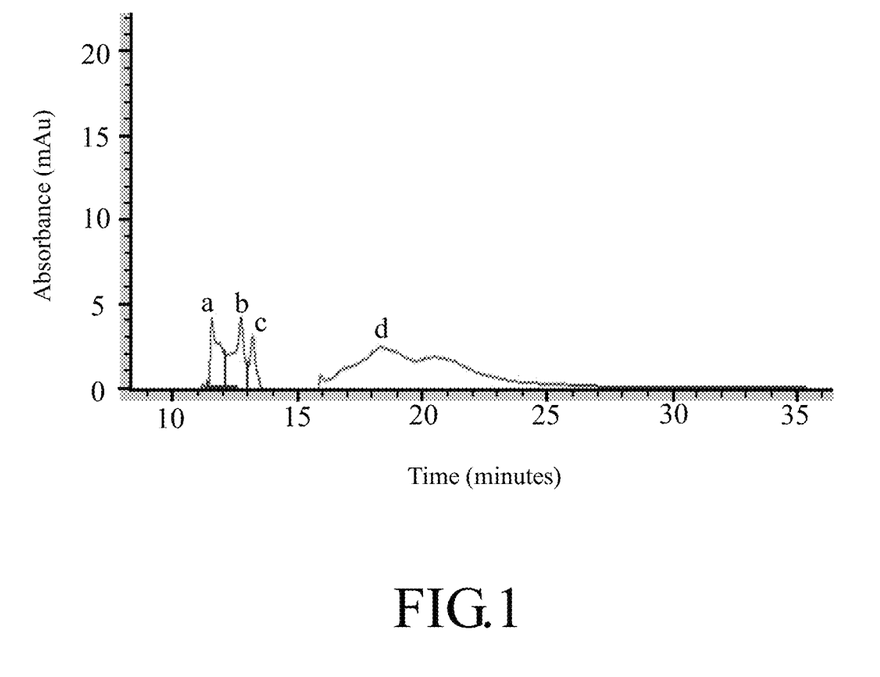
FIG. 1 is a HPLC elution profile of the HWESS (hydrolysate of water extract of *Syzygium samarangense*) prepared in Example 1.

Results:

FIG. 1 is a HPLC elution profile of the HWESS prepared in Example 1. As shown in FIG. 1, four major peaks (respectively labeled with a, b, c and d) can be observed between a retention time of 0 minute and a retention time of 35 minutes.

Example 3. Evaluation of Antioxidation Efficacy for Hydrolysate of Water Extract of *Syzygium samarangense*

In order to examine whether the HWESS according to the present disclosure has an antioxidation effect, the ferrous ion chelating ability of the HWESS prepared in Example 1 was analyzed.

Experimental Procedures:

A suitable amount of the HWESS prepared in Example 1 was dissolved in distilled deionized water, such that a HWESS sample having a HWESS concentration of 900 μg/mL was formed. 100 μL the HWESS sample, 3.7 mL of ethanol, and 0.1 mL of a 2 mM $FeCl_2 \cdot 4H_2O$ solution were mixed for 30 seconds. The resulting mixture was uniformly mixed with 0.2 mL of 5 mM ferrozine, followed by incubation in the absence of light at room temperature for 10 minutes. The absorbance at 562 nm ($OD_{562}$) was measured using a spectrophotometer (Jasco V-550). In addition, 1 mL of a 90% ethanol solution (serving as a control sample) was also subjected to the aforementioned experimental procedures. A lower $OD_{562}$ value indicates that the sample tested has a stronger antioxidation effect.

The percent ferrous ion chelation (%) was calculated using the following Equation (I):

$$A=[1-(B/C)]\times 100 \tag{I}$$

where A=the percent ferrous ion chelation (%)
B=$OD_{562}$ of the HWESS sample
C=$OD_{562}$ of the control sample All the experiments were repeated twice. The experimental data are expressed as mean±SD (standard deviation), and were analyzed by virtue of Student's test so as to assess the difference between the HWESS sample and the control sample. Statistical significance is indicated by $p<0.05$.

Figure 2:
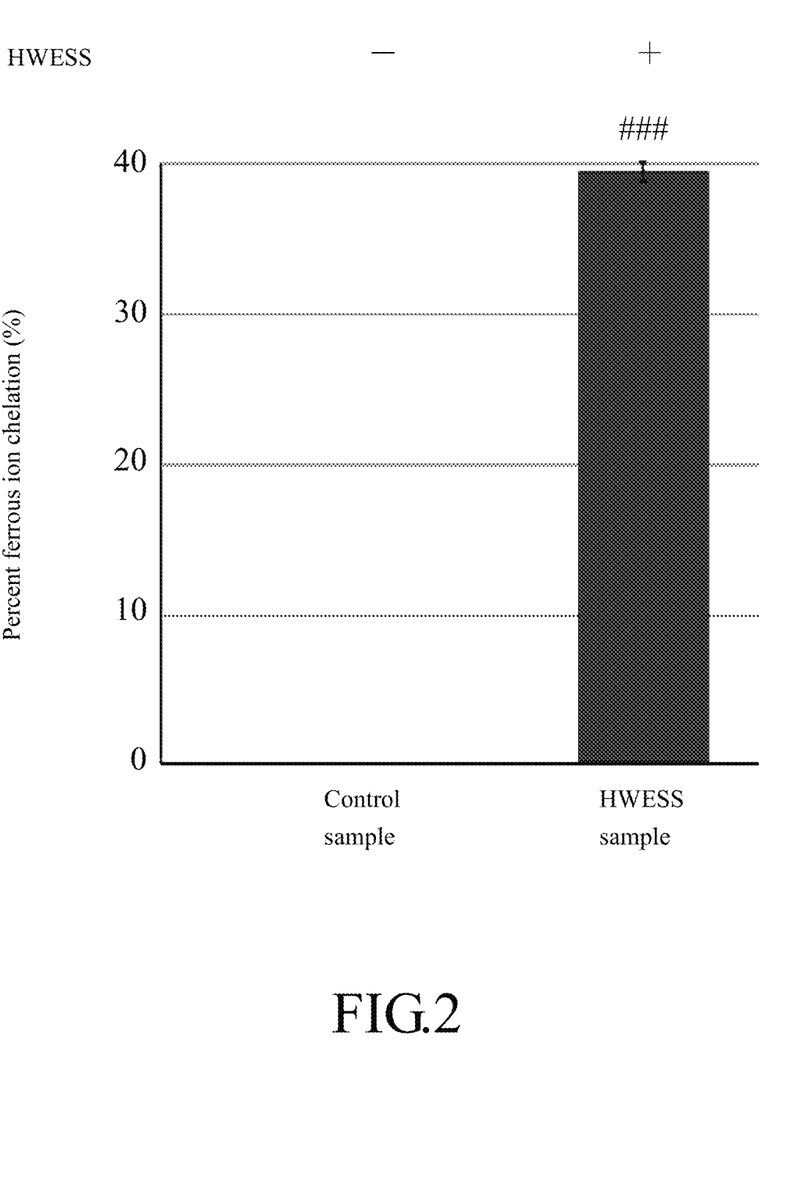
FIG. 2 shows the ferrous ion chelating ability of the HWESS prepared in Example 1, in which the symbol "###" represents $p<0.001$ (compared with the control sample).

Results:

FIG. 2 shows the percent ferrous ion chelation of the HWESS sample and the control sample. As shown in FIG. 2, the percent ferrous ion chelation of the HWESS sample is significantly higher than that of the control sample. Based on the result, the applicants deem that the hydrolysate of water extract of *Syzygium samarangense* according to the present disclosure is able to exhibit a satisfactory antioxidation effect.

Example 4. Evaluation of Melanogenesis Inhibitory Effect for Hydrolysate of Water Extract of *Syzygium samarangense*

In this example, the melanogenesis inhibitory effect of the HWESS according to the present disclosure was evaluated based on tyrosinase activity. Furthermore, for the purpose of comparison, the WESS prepared in Example 1 was subjected to the same experiment as the HWESS.

Experimental Procedures:

500 mL of a 0.1 M $Na_2HPO_4$ solution and 500 mL of a $KH_2PO_4$ solution were mixed, followed by adjusting the pH of the resulting phosphate buffer solution to 6.8 with NaGH. A suitable amount of tyrosine (Alfa Aesar, Lot: 10174330) was added into a suitable amount of the phosphate buffer solution so as to prepare a 2 mM tyrosine solution.

Subsequently, a suitable amount of a respective one of the HWESS and WESS prepared in Example 1 was added into a suitable amount of the phosphate buffer solution, such that a HWESS sample having a HWESS concentration of 10 mg/mL and a WESS sample having a WESS concentration of 10 mg/mL were obtained. 21.6 μL of a respective one of the HWESS and WESS samples was well mixed with 250 μL of tyrosinase (Sigma, Lot: SLBJ5647V) (115.42 U/mL, in a suitable amount of the phosphate buffer solution) and 540 μL of the tyrosine solution. The resultant mixture was incubated at 37° C. in the absence of light for 30 minutes. Afterward, the absorbance at 475 nm ($OD_{475}$) was measured using the spectrophotometer. Furthermore, a 290 μL of the phosphate buffer solution (serving as a control sample) was also subjected to the aforementioned experimental procedures. A lower $OD_{475}$ value indicates that the sample tested has a stronger tyrosinase inhibitory activity.

The percent tyrosinase activity inhibition (%) was calculated using the following Equation (II):

$$D=[1-(E/F)]\times 100 \tag{II}$$

where D=the percent tyrosinase activity inhibition (I)
E=$OD_{475}$ of a respective one of the HWESS, WESS and control samples
F=$OD_{475}$ of the control sample All the experiments were repeated twice. The experimental data are expressed as mean±SD, and were analyzed by virtue of Student's test so as to assess the difference between the HWESS sample, the WESS sample, and the control sample. Statistical significance is indicated by $p<0.05$.

Figure 3:
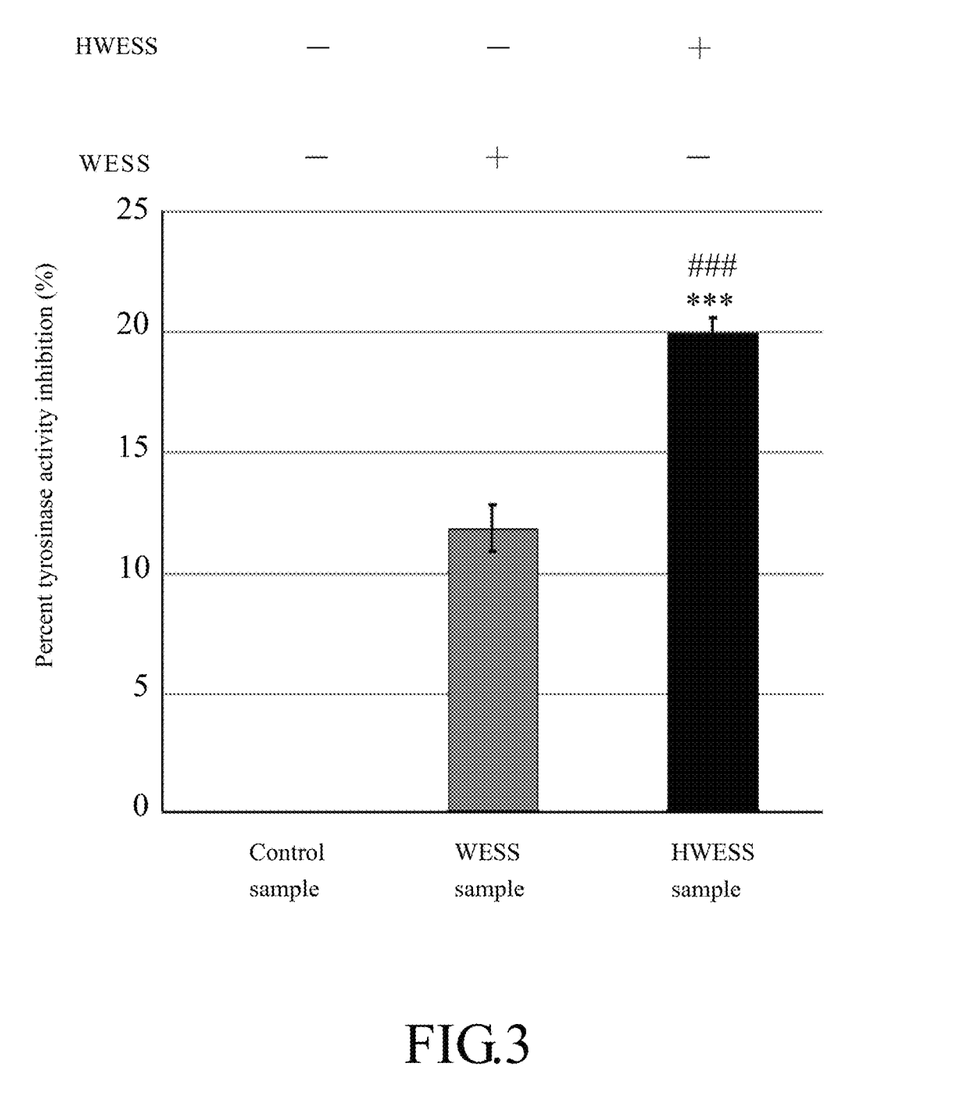
FIG. 3 shows the tyrosinase activity inhibitory effect of the HWESS and WESS (water extract of *Syzygium samarangense*) prepared in Example 1, in which the symbol "###" represents $p<0.001$ (compared with the control sample), and the symbol "***" represents $p<0.001$ (compared with the WESS sample).

Results:

FIG. 3 shows the percent tyrosinase activity inhibition of the HWESS sample, the WESS sample, and the control sample. As shown in FIG. 3, the percentage percent tyrosinase activity inhibition of the HWESS sample is significantly higher than that of each of the WESS sample and control sample. The experimental result indicates that the hydrolysate of water extract of *Syzygium samarangense* according to the present disclosure has a better tyrosinase inhibitory ability compared to the water extract of *Syzygium samarangense*. Accordingly, the applicants deem that the hydrolysate of water extract of *Syzygium samarangense* according to the present disclosure can inhibit melanogenesis by suppressing tyrosinase activity, thereby having a skin whitening effect.

Example 5. Evaluation of Improvement Effect on Wound Healing for Hydrolysate of Water Extract of *Syzygium samarangense*

In this example, the improvement effect of the HWESS according to the present disclosure on wound healing was evaluated by virtue of wound-healing cell migration assay. In addition, for the purpose of comparison, the WESS prepared in Example 1 was subjected to the same evaluation.

Experimental Materials:

A. Human Skin Fibroblast Cell Line Detroit 551

Human skin fibroblast cell line Detroit 551 used in this example was purchased from Biosource Collection and Research Center (BCRC) of Food Industry Research and Development Institute (FIRDI) (331 Shih-Pin Road, Hsinchu 300, Taiwan).

Detroit 551 cells were incubated in a Petri dish containing a minimum essential medium (MEM; Sigma, Product No.: M2279) supplemented with 10% fetal bovine serum (FES) and 1% penicillin-streptomycin (Gibco™, Cat. No.: 15140122), followed by cultivation in an incubator (37° C., 5% $CO_2$). Medium change was performed every two days. Cell passage was performed when the cultured cells reached 80%-90% of confluence.

Experimental Procedures:

The Detroit 551 cells were divided into 3 groups including a HWESS group, a WESS group, and a control group. Each group of the Detroit 551 cells was incubated in a 24-well plate containing 500 μL of MEM (supplemented with 10% PBS and 1% penicillin-streptomycin) at $2\times10^5$ cells/well, followed by cultivation in an incubator (37° C., 5% $CO_2$) for 24 hours.

After medium change with a fresh medium, a plastic pipette tip of 200 μL was used to scratch the Detroit 551 cells in each well of the plate along a diametral line. Therefore, a wound zone having a width of 500 μm and no cells attached thereto was formed along a diametral line of each well. Washing was conducted with phosphate buffered saline (PBS) twice. After medium change was performed with a fresh MEM (supplemented with 0.5% PBS and 1% penicillin-streptomycin), the cell cultures of the HWESS and WESS groups were respectively treated with suitable amounts of the HWESS and WESS prepared in Example 1, so that the cell cultures of the HWESS and WESS groups respectively had final concentrations of 0.03% (w/w) HWESS and 0.03% (w/w) WESS The cell culture of the control group received no treatment.

Subsequently, cultivation was conducted in an incubator (37° C., 5% $CO_2$) for 12 hours. At 0 hour (i.e. before the treatment) and 12 hour after the treatment, the wound zones of each group were observed using an inverted microscope (NIKON TE300, Japan) under 40× magnification, were photographed using a digital camera (Nikon F90, Japan), and were subjected to area calculation according to the photographs obtained using ImageJ software.

The wound healing percentage (%) was calculated using the following Equation (III):

$$G=[1-(H/I)]\times 100 \qquad (III)$$

where G=the wound healing percentage (%)
H=the area of the wound zone at 12 hour after the treatment
I=the area of the wound zone at 0 hour All experiments were repeated twice. The experimental data are expressed as mean±SD, and were analyzed by virtue of Student's test so as to assess the difference between the HWESS group, the WESS group, and the control group. Statistical significance is indicated by $p<0.05$.

Figure 4:
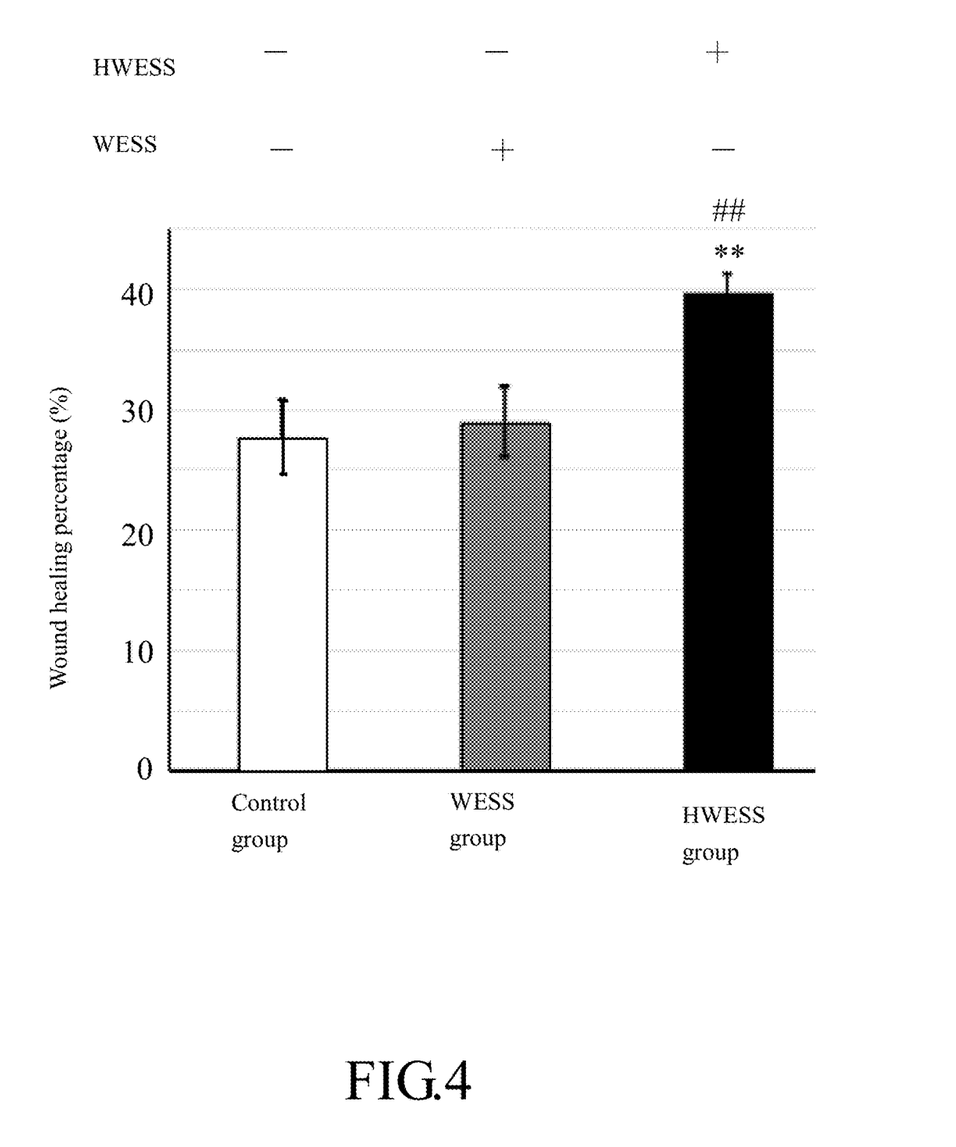
FIG. 4 shows the improvement effect of the HWESS and WESS prepared in Example 1 on wound healing, in which the symbol "##" represents $p<0.01$ (compared with the control group), and the symbol "**" represents $p<0.01$ (compared with the WESS group).

Results:

FIG. 4 shows the wound healing percentage of the Detroit 551 cells treated with HWESS and WESS, and those receiving no treatment. As shown in FIG. 4, there is no significant difference in the wound healing percentage between the WESS group and the control group. However, the wound healing percentage of the HWESS group is significantly higher than that of each of the control group and the WESS group. The experimental results reveal that the hydrolysate of water extract of Syzygium samarangense according to the present disclosure is effective in improving fibroblast-mediated wound closure, thereby being able to facilitate wound healing.

Example 6. Evaluation of Enhancement Effect on Moisture-Retaining Capacity of Skin for Hydrolysate of Water Extract of Syzygium samarangense In order to investigate the enhancement effect of the HWESS according to this disclosure on the moisture-retaining capacity of human skin, the following experiments were performed.

A. Preparation of Essences

The HWESS and the WESS prepared in Example 1 were used in this example. Three essences (including a HWESS essence, a WESS essence and a control essence) were respectively formulated using the recipes shown in Table 1.

TABLE 1

| Ingredients | HWESS essence | WESS essence | Control essence |
|---|---|---|---|
| Butylene glycol# | 1 | 1 | 1 |
| Hydroxyethyl cellulose# | 0.3 | 0.3 | 0.3 |
| Dermosoft OMP* | 3 | 3 | 3 |
| HWESS | 4 | — | — |
| WESS | — | 4 | — |
| Deionized water | 91.7 | 91.7 | 95.7 |

The amount of each ingredient is expressed as % (w/w).
purchased from First Chemical Co., Ltd.
*purchased from HonorChem Co., Ltd.

The process for formulating the HWESS essence and the WESS essence is described in more detail as follows. Butylene glycol and hydroxyethyl cellulose were dissolved in deionized water at 75° C. under agitation, followed by cooling to 40° C.-45° C. A respective one of the HWESS and the WESS was added, followed by mixing with Dermasoft OMP under agitation. Then, NaOH was used to adjust the pH of the resulting mixture to about 6 to 7. Thus, the HWESS essence and the WESS essence were obtained.

The process for formulating the control essence is similar to that for formulating the HWESS essence, except that additional deionized water was used instead of the HWESS.

B. Screening of Test Subjects

Subjects enrolled from Yeun Diing Enterprise CO., LTD. (Pingtung county, Taiwan) and M.H. Biotechnology Co., Ltd. (Yunlin County, Taiwan) were subjected to screening according to the exclusion criteria outlined in Table 2. A total of 10 eligible test subjects, including 4 males and 6 females at an age ranging from 25 to 40 years, participate in the following test.

TABLE 2

| No. | Exclusion criteria |
|---|---|
| 1 | Possession of sensitive skin |
| 2 | Possession of a skin disease, such as eczema, atopic dermatitis and allergic dermatitis |
| 3 | Pregnancy |
| 4 | Use of other skin care product(s) containing a moisture-retaining ingredient during the test |

C. Application of Test Essences

The right arm of each of the test subjects was randomly divided into three test areas having a width of 4 fingerbreadths (i.e. a HWESS area, a WESS area and a control area), onto which the HWESS essence, the WESS essence, and the control essence prepared in section A of this example were respectively applied at a dose of 0.5 mL twice daily. The test period for each test area lasted for a total of 28 days.

D. Determination of Water Content of Stratum Corneum

On Day 0 (i.e. prior to the application of the test essences) and at a designated time point after the beginning of the application of the test essences (Days 7, 14, 21 and 28), the test areas on each test subject were separately subjected to determination of the water content of stratum corneum using a capacitance meter (Corneometer® CM 285, Courage & Khazaka).

The percent improvement of the water content of stratum corneum (%) was calculated using the following Equation (IV):

$$J=[(L-K)/K]\times 100 \quad (IV)$$

where J=the percent improvement of the water content of stratum corneum (%) at the designated time point (Days 14, 21 and 28)
K=the water content of stratum corneum on Day 0
L=the water content of stratum corneum at the designated time point The test areas on each test subject were repeatedly subjected to the water content determination 3 times. The experimental data are expressed as mean±SD, and were analyzed by virtue of Student's test so as to assess the difference between the test areas. Statistical significance is indicated by $p<0.05$.

E. Safety Evaluation

Safety evaluation was conducted by a researcher on Day 0 and at the designated time point thereafter (Days 7, 14, 21 and 28). On Day 0, small amounts of the essences were applied onto an inner side of an upper arm portion for safety evaluation only. The test subjects were surveyed by the researcher in respect to the occurrence of any adverse skin response (including itchiness, irritation and erythema).

Results:

A. Determination of Water Content of Stratum Corneum

Figure 5:
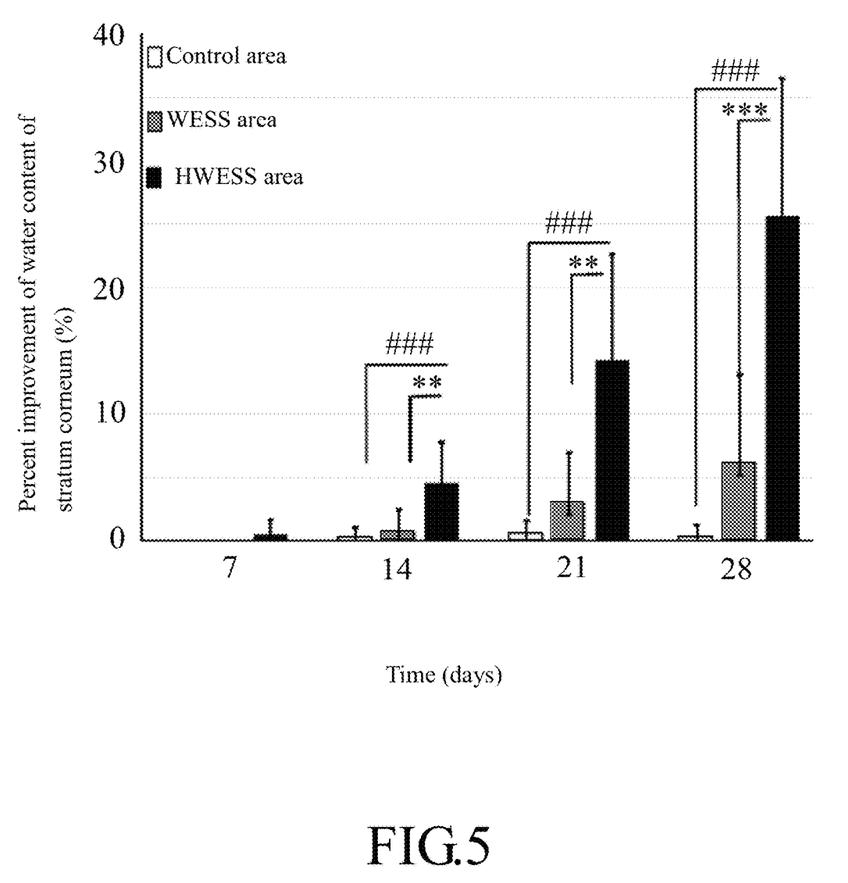
FIG. 5 shows the improvement effect of the HWESS and WESS prepared in Example 1 upon the water content of stratum corneum, in which the symbol "###" represents $p<0.001$ (compared with the control area), and the symbols "* *" and "* * *" respectively represent $p<0.01$ and $p<0.001$ (compared with the WESS area).

FIG. 5 shows the percent improvement of the water content of stratum corneum in each test area at different time points. As shown in FIG. 5, on Days 14, 21 and 28 after the beginning of the application of the test essences, the percent improvement of the water content of stratum corneum in the HWESS area is significant higher than that in each of the WESS area and the control area. In addition, the water content of stratum corneum in the HWESS area dramatically increased with time, while the improvement of water content in the WESS test area was quite slow. These data suggest that the hydrolysate of water extract of *Syzygium samarangense* according to the present disclosure can be used to effectively enhance the moisture-retaining capacity of skin.

B. Safety Evaluation

During the test period, no adverse skin response was observed on all the test subjects (data not shown).

In view of the foregoing, the hydrolysate of water extract of *Syzygium samarangense* according to the present disclosure can exhibit an excellent antioxidation activity, inhibit melanogenesis, enhance the moisture-retaining capacity of skin, and promote wound healing. Therefore, the applicants deem that the hydrolysate of water extract of *Syzygium samarangense* according to the present disclosure can be developed into a skin care product for long-term use which does not induce adverse side effects All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A process for preparing a hydrolysate of water extract of *Syzygium samarangense*, comprising:
    subjecting a fruit material of *Syzygium samarangense* to an extraction treatment with water so as to obtain a water extract; and
    subjecting the water extract to a hydrolysis treatment with bromelain.

2. The process of claim 1, wherein the weight ratio of the fruit material of *Syzygium samarangense* to water ranges from 1:0.5 to 1:5.

3. The process of claim 1, wherein the weight ratio of the bromelain to the water extract ranges from 1:50 to 1:300.

4. The process of claim 1, further comprising conducting a solid-liquid separation treatment after the hydrolysis treatment so as to remove a solid portion resulting from the hydrolysis treatment.

5. The process of claim 1, wherein the fruit material of *Syzygium samarangense* comprises a pulp of *Syzygium samarangense*.

6. The process of claim 5, wherein the fruit material of *Syzygium samarangense* further comprises a peel of *Syzygium samarangense* and a seed of *Syzygium samarangense*.

7. A hydrolysate of water extract of *Syzygium samarangense*, which is prepared by a process comprising:
    subjecting a fruit material of *Syzygium samarangense* to an extraction treatment with water so as to obtain a water extract; and
    subjecting the water extract to a hydrolysis treatment with bromelain.

8. The hydrolysate as claimed in claim 7, wherein the weight ratio of the fruit material of the *Syzygium samarangense* to water ranges from 1:0.5 to 1:5.

9. The hydrolysate as claimed in claim 7, wherein the weight ratio of bromelain to the water extract ranges from 1:50 to 1:300.

10. The hydrolysate as claimed in claim 7, wherein the process further comprises conducting a solid-liquid separation treatment after the hydrolysis treatment so as to remove a solid portion resulting from the hydrolysis treatment.

11. The hydrolysate as claimed in claim 7, wherein the fruit material of *Syzygium samarangense* comprises a pulp of *Syzygium samarangense*.

12. The hydrolysate as claimed in claim 11, wherein the fruit material of *Syzygium samarangense* further comprises a peel of *Syzygium samarangense* and a seed of *Syzygium samarangense*.

13. A composition comprising a hydrolysate according to claim 7.

14. The composition as claimed in claim 13, which is for whitening skin.

15. The composition as claimed in claim 13, which is for enhancing the moisture-retaining capacity of skin.

16. The composition as claimed in claim 13, which is for improving wound healing.

17. The composition as claimed in claim 13, which is for reducing oxidative stress.

18. The composition as claimed in claim 13, the composition being in a topical dosage form.

19. The composition as claimed in claim 13, the composition being in an oral dosage form.

* * * * *